United States Patent [19]

Zaromb

[11] Patent Number: 4,912,051
[45] Date of Patent: Mar. 27, 1990

[54] PERMEATION ABSORPTION SAMPLER WITH MULTIPLE DETECTION

[75] Inventor: Solomon Zaromb, Hinsdale, Ill.
[73] Assignee: The United States of America as represented by the United States Department of Energy, Washington, D.C.
[21] Appl. No.: 330,654
[22] Filed: Mar. 30, 1989

Related U.S. Application Data

[63] Continuation-in-part of Ser. No. 892,990, Aug. 4, 1986, Pat. No. 4,829,008.

[51] Int. Cl.⁴ .............................................. G01N 1/18
[52] U.S. Cl. ...................... 436/178; 436/52; 436/53; 436/54; 436/55; 436/165; 436/167; 436/168; 436/172; 436/909; 422/52; 422/86; 422/88; 422/91; 422/56; 422/89; 422/98; 55/16; 55/158
[58] Field of Search .............. 436/178, 161, 165, 169, 436/170, 168, 52, 53, 172, 167, 54, 55, 909; 422/69, 70, 52, 53, 56, 86, 88, 89, 91, 98; 55/16, 158, 18, 67, 386; 73/61.1 C, 863.23, 863.03, 863.71

[56] References Cited

U.S. PATENT DOCUMENTS

| | | | |
|---|---|---|---|
| 3,352,644 | 11/1967 | Lysyj | 436/178 X |
| 3,751,879 | 8/1973 | Allington | 55/158 |
| 4,311,789 | 1/1982 | Nylen et al. | 436/178 X |
| 4,529,521 | 7/1985 | Cortes et al. | 436/161 X |
| 4,569,918 | 2/1986 | Moore et al. | 436/178 X |
| 4,701,306 | 10/1987 | Lawrence et al. | 436/178 X |
| 4,829,008 | 5/1989 | Zaromb | 422/69 X |

FOREIGN PATENT DOCUMENTS 130994  10/1979  Japan .................................. 436/178

OTHER PUBLICATIONS

Siemer et al., "Silicone Rubber Tubing for Elimination of Background Conductivity in Anion Chromatography", Analytical Chemistry 1984, vol. 56, p. 1,033.
Siemer et al., "Carbon Dioxide Permeable Tubing for Post-Suppression in Ion Chromatography", Analytical Chemistry, 198, vol. 56, pp. 1085, 1089.
Tanner et al., "Sampling and Determination of Gas—Phase Hydrogen Peroxide Following Removal of Ozone by Gas-Phase Reaction with Nitric Oxide", Analytical Chemistry, vol. 58, Jul. 1986, pp. 1858–1865.
Zaromb et al., "Technique for Calibrating Air Samplers and Certain Other Analytical Devices", Journal of Chromatography, vol. 438, pp. 100–102 (Apr. 1, 1988).
Zaromb et al., "Simple Permeation Absorber for Sampling and Preconcentrating Hazardous Air Contaminants", Journal of Chromatography, vol. 439, pp. 283–299 (May 20, 1988).
Zaromb, "Preconcentrating Air Sampler—PAS-100", Tech. Notes, p. 621 (NTIS, Jul. 1988).
Kandallu, "An Evaluation of a Permeation–Absorption–Type Preconcentrator Sampler in the Measurement of Low Concentrations of Hydrazine", (1988).

*Primary Examiner*—Barry S. Richman
*Assistant Examiner*—Lynn M. Kummert
*Attorney, Agent, or Firm*—Hugh W. Glenn; Robert J. Fisher; William R. Moser

[57] ABSTRACT

A system for detecting analytes in air or aqueous systems includes a permeation absorption preconcentrator sampler for the analytes and analyte detectors. The preconcentrator has an inner fluid-permeable container into which a charge of analyte-sorbing liquid is intermittently injected, and a fluid-impermeable outer container. The sample is passed through the outer container and around the inner container for trapping and preconcentrating the analyte in the sorbing liquid. The analyte can be detected photometrically by injecting with the sorbing material a reagent which reacts with the analyte to produce a characteristic color or fluorescence which is detected by illuminating the contents of the inner container with a light source and measuring the absorbed or emitted light, or by producing a characteristic chemiluminescence which can be detected by a suitable light sensor. The analyte can also be detected amperometrically. Multiple inner containers may be provided into which a plurality of sorbing liquids are respectively introduced for simultaneously detecting different analytes. Baffles may be provided in the outer container. A calibration technique is disclosed.

20 Claims, 6 Drawing Sheets

PERMEATION ABSORPTION SAMPLER WITH MULTIPLE DETECTION

CONTRACTUAL ORIGIN OF THE INVENTION

The United States government has rights in this invention pursuant to Contract No. W-31-109-ENG-38 between the U.S. Department of Energy and The University of Chicago representing Argonne National Laboratory.

REFERENCE TO RELATED APPLICATION

This is a continuation-in-part of copending U.S. application Ser. No. 892,990, filed Aug. 4, 1986, entitled "Analytical Instrument with Apparatus and Method for Sample Concentrating", now U.S. Pat. No. 4,829,008, the disclosure of which is incorporated herein by reference.

BACKGROUND OF THE INVENTION

The present invention relates to analytical instruments for detecting and identifying trace levels of selected vapors, and i particular to portable instruments. The present invention has particular application to detection and identification of various vapors in gaseous media, such as air.

It is known to preconcentrate analytes in air samples by the use of sorbents, and thereby increase the sensitivity of detecting instruments. The aforementioned copending U.S. application Ser. No. 828,990 discloses the use of an absorption preconcentrating air sampler to increase the sensitivity of an analytical instrument. In such a sampler, a substantial portion of the analyte contained in a large volume of air becomes absorbed in a small volume of liquid extractant that can be injected directly into an analytical instrument, such as a liquid chromatograph. As compared with other methods, the direct absorption of an analyte from an arbitrarily large volume of air into a small volume of liquid extractant offers the advantages of low-temperature operation, simplicity, speed and flexibility. That device has proved effective for detecting hazardous analytes, such as highly carcinogenic primarily aromatic amines, when used with gas or liquid chromatographs.

It is also known to colorimetrically detect analytes by the use of Draeger tubes, in which selected reagents change color in predetermined ways in response to certain analytes. But the Draeger tubes are of relatively low sensitivity, utilizing a relatively large volume of reagent, and can effect measurements over a limited concentration range. Furthermore, this technique is of limited flexibility, since it is not easily adapted to frequent repetitive measurements.

SUMMARY OF TEE INVENTION

It is a general object of the present invention to increase the applicability of the absorption preconcentrating sampler of the aforementioned copending U.S. application Ser. No. 892,990 by coupling in with other types of analytical techniques to effect detection of a wide variety of analytes.

An important feature of the invention is the provision o an analytical system that is portable, and is yet capable of efficiently analyzing trace concentrations of selected vapors in air, at concentrations ranging from ppm (parts per million) levels to ppb (parts per billion) levels.

In connection with the foregoing feature, it is another feature of the invention to provide a system of the type set forth, which effects a turbulent flow of air through the preconcentration sampler to maximize absorption of the analyte.

Another feature of the invention is the provision of an analytical system of the type set forth, which utilizes colorimetric detection with high sensitivity and a wide measurable concentration range.

In connection of the foregoing feature, still another feature of the invention is the provision of an analytical system of the type set forth, which may be easily adapted to frequent repetitive measurements.

Anther feature of the invention is the provision of the system of the type set forth, which permits simultaneous sampling and/or monitoring of several different analytes.

Another feature of the invention is the provision of a self-sufficient monitor for analytes of interest.

Still another feature of the invention is the provision of a calibration technique for systems of the type set forth.

These and other features of the invention are attained by providing a system for detecting traces of an analyte in a fluid medium comprising: permeation absorption preconcentrator means having a fluid-impermeable outer container and a fluid-permeable inner container, injection means for introducing analyte-sorbing material into the inner container, flow means for flowing the fluid medium through the outer container and around the inner container for trapping traces of analyte in the sorbing material, detection means coupled to the sorbing material containing traces of analyte trapped therein and responsive to the analyte for producing an output signal, and control means coupled to the injection means and to the flow means and to the detection means for controlling the operations thereof.

Additional objects, advantages and novel features of the invention will be set forth in part in the description which follows, and in part will become apparent to those skilled in the art upon examination of the following drawings or may be learned by practicing the invention. The objects and advantages of the invention may be realized and attained by means of the instrumentalities and combinations particularly pointed out in the appended claims.

BRIEF DESCRIPTION OF THE DRAWINGS

For the purpose of facilitating an understanding of the invention there are illustrated in the accompanying drawings preferred embodiments thereof, from an inspection of which, when considered in connection with the following description, the invention, its construction and operation, and many of its advantages should be readily understood and appreciated.

DESCRIPTION OF THE PREFERRED EMBODIMENTS

Figure 1:
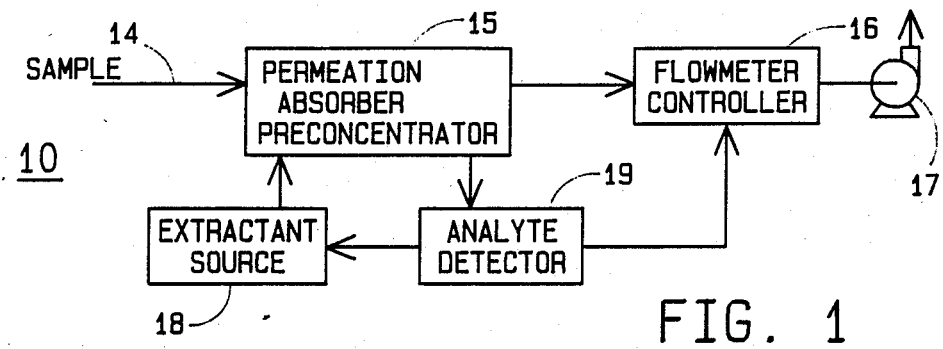
FIG. 1 is a functional block diagram illustrating an analytical system using a permeation absorption sampler in accordance with the present invention.

Referring to FIG. 1, there is illustrated a generalized analytical system 10 in accordance with the principles of the present invention. The system 10 includes a preconcentrator 15, in the form of a permeation absorber, which may be of the type disclosed in the aforementioned copending U.S. application Ser. No. 892,990. More specifically, the preconcentrator 15 includes an inner fluid-permeable container and an outer fluid-impermeable container. The preconcentrator 15 has a fluid inlet 14 and a fluid outlet which is coupled through a flowmeter controller 16 to a pump 17. The system 10 also includes an extractant source 18 which is coupled to the preconcentrator 15 and provides analyte-sorbing liquid thereto. Also coupled to the preconcentrator 15 is an analyte detector 19. The output signal from the analyte detector 19 may be coupled to the extractant source 18 and to the flowmeter controller 16.

In operation, the fluid medium to be sampled, which contains traces of the analyte of interest, is drawn in through the inlet 14 into the outer container of the preconcentrator 15, flowing around the inner container and thence outwardly through the flowmeter controller 16 and pump 17. The analyte-sorbing liquid, which is selected to preferentially absorb the analyte of interest, is injected from the extractant source 18 into one end of the inner container of the preconcentrator 15 in which it absorbs traces of the analyte of interest in the sample medium flowing around the inner container. The analyte-enriched sorbing liquid then passes to the analyte detector 19, which produces a signal indicative of the presence of the analyte of interest.

If the output signal from the analyte detector 19 is too small, the frequency with which analyte-sorbing liquid is injected into the preconcentrator 15 may be decreased, thereby increasing its residence time in the preconcentrator 15 and/or the flowmeter controller 16 may be activated to increase the speed of the pump 17, thereby increasing the rate of flow of sample medium through the preconcentrator 15 to accordingly increase the volume of medium sampled per unit time period. On the other hand, if the output signal from the analyte detector 19 is too large, the frequency of injection of the analyte-sorbing liquid from the extractant source 18 may be increased and/or, the pump 17 may be slowed.

Figure 2:
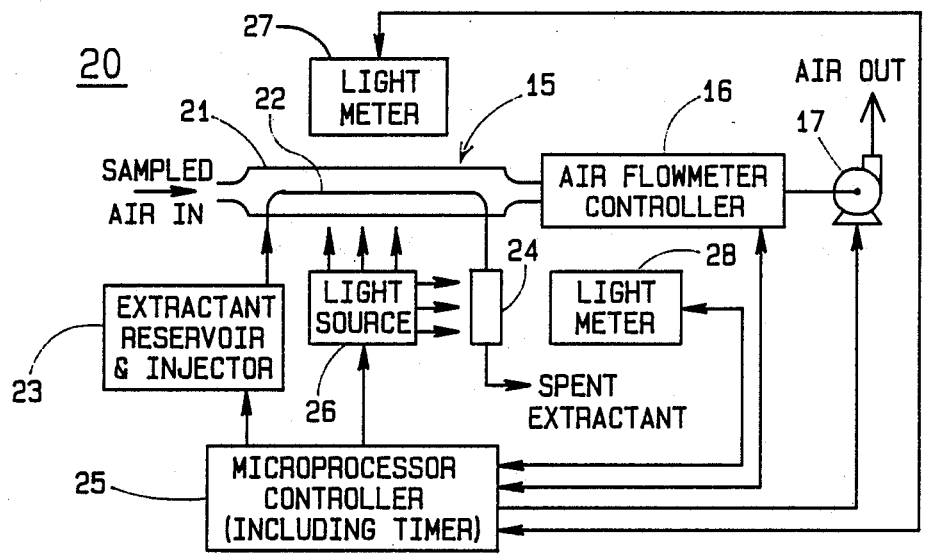
FIG. 2 is a functional bock diagram of an analytical system constructed in accordance with one embodiment of the present invention utilizing colorimetric detection.

While the analyte detector 19 may be a separate and discrete detection unit, such as a chromatograph or a mass spectrometer, the present invention is particularly advantageous when used with an analyte detector which may be self-contained with the preconcentrator 15 in a portable system. Referring to FIG. 2, there is illustrated an analytical system 20 in accordance with the present invention, which utilizes photometric analyte detection and, in particular, colorimetric detection. The system 20 includes the preconcentrator 15, which has a gas-impermeable outer container 21 and a gas-permeable inner container 22. The sample gaseous medium, typically air, is drawn in through the air inlet of the outer container 21, passes around the inner container 22 and lows out through the air outlet and the air flowmeter controller 16 to the pump 17. An extractant reservoir and injector 33 is coupled to the inlet end of the inner container 22 and the outlet end thereof is coupled through a collection vessel 24 to a spent extractant reservoir.

The system 20 includes a microprocessor controller 25 which includes a suitable timer. The microprocessor controller 25 is coupled to the flowmeter controller 16 for receiving output signals therefrom and for transmitting control signals thereto. The microprocessor controller 25 also has an output coupled to the pump 17, and has another output coupled to the extractant reservoir and injector 23 and another coupled to a light source 26. Preferably, the inner and outer containers 21 and 22 of the preconcentrator 15 and the collection vessel 24 are transparent or translucent to the light emitted from the light source 26. Light from the source 26 is transmitted through the preconcentrator 15 and the collection vessel 24 to light meters 27 and 28, respectively. The microprocessor controller 25 is coupled to the light meters 27 and 28 for receiving output signals therefrom and transmitting control signals thereto. The light meters 27 and 28 include light filters (not shown) having transmission bands which match the absorption band of the color that is generate by a selected colorimetric reagent in the presence of a selected analyte.

In operation, the air to be sampled is drawn through the preconcentrator 15 in the same manner described above with respect to FIG. 1. The reservoir and injector 23 injects into the inner container 22 of the preconcentrator 15 a combination of analyte-sorbing liquid and reagent tailored to the analyte of interest. More specifically, the sorbing liquid is designed to preferentially absorb the analyte, while the reagent is responsive to the analyte to produce a chemical reaction which results in a predetermined color change. Thus, as the analyte is absorbed in the sorbing liquid in the inner container 22, it react with the reagent to produce the desired color change, which is made visible by illumination of the inner container 22 and the contents thereof by the light source 26. The color change is detected by the light meter 27, which may serve to provide a "coarse" measurement of the color change.

If a color change is detected by the light meter 27, the sample may be transferred from the inner container 22 to the collection vessel 24, in which it is again illuminated by the light source 26, the color change being detected by the light meter 28, which provides a more accurate reading of the amount of color change. It will be appreciated that the transfer of the analyte-enriched sorbing liquid from the inner container 22 to the collection vessel 24 is effected by the injection of a new volume of sorbent/reagent into the inner container 22 for displacing the previous volume into the collection vessel 24. This transfer is controlled by the microprocessor controller 25 in response to an output signal from the light meter 27.

In an alternative mode of operation, the light meter 27 may be dispensed with, and the reservoir and injector 23 may be controlled by the microprocessor controller 25 to inject predetermined volumes of sorbent/reagent into the inner container 22 at predetermined time intervals, which are selected to be sufficiently long to permit a measurable amount of the analyte to be absorbed into the sorbing liquid. As each analyte-enriched volume of sorbent is passed into the collection vessel 24, the analyte therein is detected by the light meter 28. The microprocessor controller 25 may measure the difference between the output signals from the light meter 28 in response to consecutive volumes of sorbent.

As was explained above in connection with FIG. 1, if the output signal from the light meter 28 is too small, the microprocessor controller 25 operates to decrease the frequency of sorbent injection and/or increase the speed of the pump 17. On the other hand, if the output signals from the light meter 28 are too high, the microprocessor controller 25 operates to increase the frequency of sorbent injection and/or to decrease the speed of the pump 17.

More than seventy selective color indicating reactions are available with Draeger tubes for a large number of compounds, many of which may be of interest, including acrylorinitrile, aniline, arsine, benzene, ethylene oxide, formaldehyde, hydrazine, mercury vapor, phosgene, phosphine, and vinyl chloride. Although designed for Draeger tubes, these reactions may also be utilized with the preconcentrator 15. When used in the system 20, these color indicating reactions provide much higher sensitivity than Draeger tubes, resulting from the use of a smaller volume of extractant (typically about 0.1 ml, as compared with 1 g in Draeger tubes), and arbitrarily high air volumes. Furthermore, the system 20 affords a much wider measurable concentration range than Draeger tubes, achievable by measuring the air volume (or sample flow time) required to yield an observable or measurable color change. The system 20 also affords convenience and flexibility, since it is readily adapted to frequent repetitive measurements or quasi-continuous monitoring by automatically replacing the sorbing liquid either at predetermined time intervals or after a pronounced color change.

Figure 3:
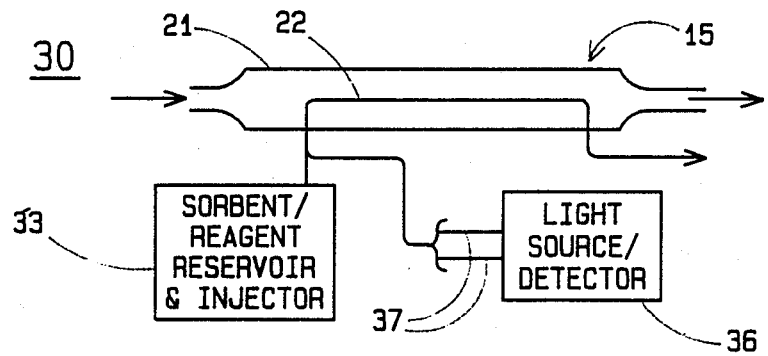
FIG. 3 is a functional block diagram of another embodiment of the present invention utilizing photometric detection with the use of optic fibers.

Referring now to FIG. 3, there is illustrated an analytical system 30, which is fundamentally similar to the system 20, but is even more readily adapted to portable applications. The system 30 includes the preconcentrator 15, which may be coupled to associated flow control devices as explained in connection with the system 20, but which have been omitted from FIG. 3 for simplicity. The system 30 also includes a sorbent/reagent reservoir and injector 33 which inject a combination of analyte-sorbing liquid and a suitable reagent tailored to the analyte of interest into the inner container 22 of the preconcentrator 15. There is also provided a light source/detector unit 36 which is coupled by optical fibers 37 to the inner container 22. More specifically, two optical fibers 37 may be respectively connected at one end thereof to the light source and to the light detector while the other ends thereof are inserted in the inner container 22 a distance sufficient to be disposed in use well within the preconcentrator 15.

In operation, the system 30 functions substantially the same as the system 20, described above, except that the analyte-enriched sorbing liquid is illuminated within the inner container 22 by one optic fiber and any color change can there be detected and transmitted by the other optic fiber to the light source/detector unit 36. It will be appreciated that in this arrangement, the outer and inner containers 21 and 22 of the preconcentrator 15 need not be transparent or translucent. If desired, the light source/detector unit 36 and the optic fibers 37 may be in the form of an optrode.

Figure 4:
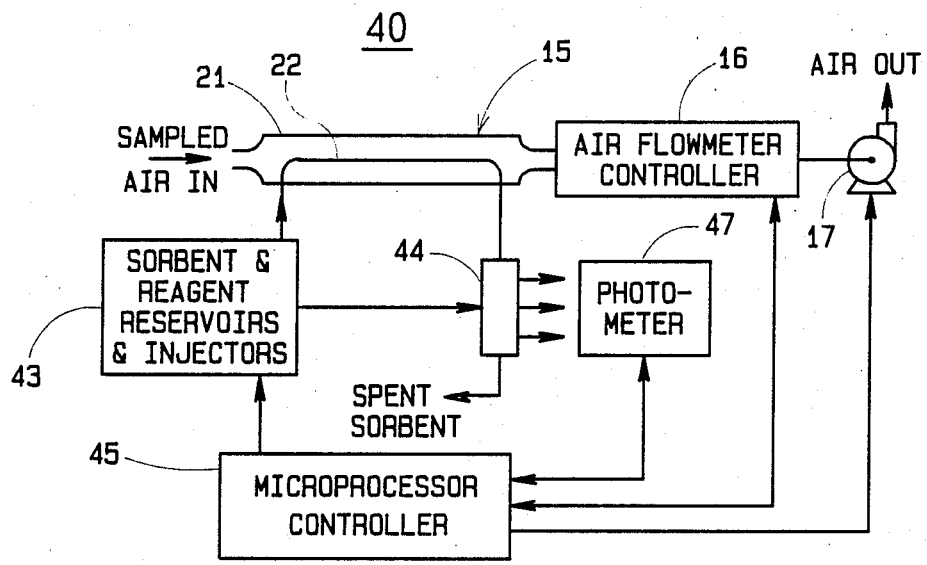
FIG. 4 is a functional block diagram of another embodiment of the invention utilizing chemiluminescence and photometric detection.

Referring now to FIG. 4, there is illustrated an analytical system 40 in accordance with the present invention, which utilizes chemiluminescent analyte detection. The system 40 includes the preconcentrator 15, the flowmeter controller 16 and the air pump 17 of the system 20 intercoupled and operating in the same manner described in connection with FIG. 20. The system 40 also includes sorbent and reagent reservoirs and injectors 43 coupled to the input end of the inner container 22 of the preconcentrator 15, the output end of which is coupled to a transparent or translucent collection vessel 44, which is also directly coupled to the sorbent and reagent reservoirs and injectors 43. A microprocessor controller 45 is coupled to the sorbent and reagent reservoirs and injectors 43, the flowmeter 16 and the pump 17 in substantially the same manner as was described above in connection with the system 20. The system 40 also includes a photometer 47, which is coupled to the microprocessor controller 45.

The system 40 operates similarly to the system 20, except that the reagent injected into the inner container 22 is a chemiluminescence-generating reagent, rather than a color-generating reagent. When the analyte-enriched sorbing material is displaced into the collection vessel 44, the reaction of the analyte with the reagent produces a chemiluminescence which is detected by the photometer 47. The reservoirs and injectors 43 may be either directly coupled to the collection vessel 44 for continuously flowing the sorbent and reagent therethrough, or else when it is desired to displace a volume of analyte-enriched sorbing liquid from the preconcentrator 15 to the collection vessel 44, the microprocessor controller 45 may operate to turn off the continuous direct flow of sorbent and reagent from the reservoirs and injectors 43 and to institute an intermittent flow, as in the afore described system 20.

It will be appreciated that the reservoirs and injectors 43 may be adapted to inject multiple different combinations of sorbents and reagents for detecting different analytes of interest. Thus, different combinations may be injected on successive injections if desired, for detecting different analytes in the gaseous medium.

Figure 5:
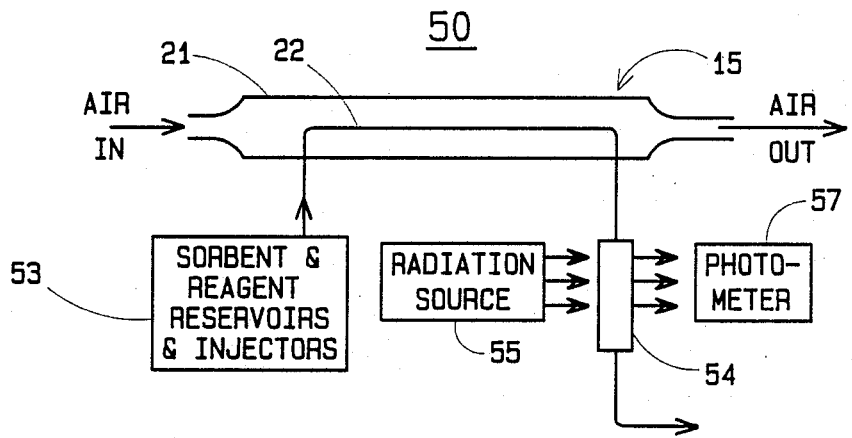
FIG. 5 is a functional block diagram of another embodiment of the invention utilizing fluorescence and photometric detection.

FIG. 5 depicts another photometric analytic system 50 which utilizes fluorescent detection of the analyte. The system 50 includes the preconcentrator 15 which may be coupled to the associated flow control devices for operation in substantially the same manner described above with respect to FIG. 4, but which have been omitted from FIG. 5 for simplicity. The system 50 includes sorbent and reagent reservoirs and injectors 53, which function substantially the same as the reservoirs and injectors 43 described above in connection wit FIG. 4, except that the reagent injected is a fluorescence-generating reagent. The analyte-enriched sorbing liquid from the preconcentrator 5 is fed to a transparent or translucent collection vessel 54 which is illuminated by a radiation source 55, which emits a radiation of a type suitable for causing the product of the analyte/reagent reaction to fluoresce. The light emitted is detected by a photometer 57.

Figure 6:
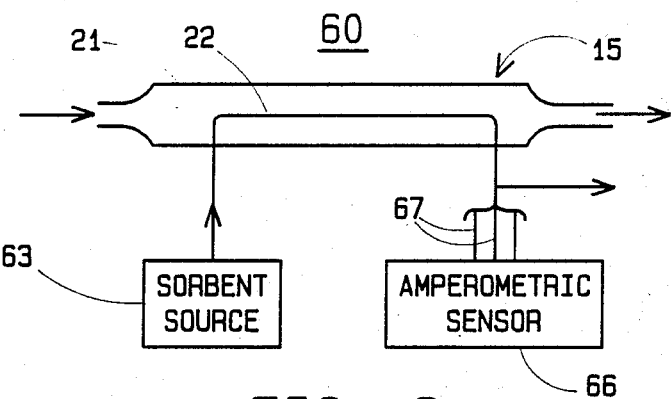
FIG. 6 is a functional block diagram of another embodiment of the invention utilizing amperometric detection.

In FIG. 6, there is illustrated an analytical system 60 in accordance with the present invention which utilizes amperometric sensing of the analyte. The system 60 is similar to the system 30, described above, and includes a preconcentrator 15 and a sorbent source 63 which is coupled to the inlet end of the inner container 22 of the preconcentrator 15 for introducing thereinto an analytesorbing liquid designed to preferentially absorb the analyte of interest. There is also provided an amperometric sensor 66 having plural electrodes 67, which may be microelectrodes, and which are inserted into the inner container 22 of the preconcentrator 15. It will be appreciated that the preconcentrator 15 may be coupled to associate flow control equipment, as was described above with respect to FIG. 2, but which is omitted from FIG. 6 for simplicity. The electrodes 67 typically include a reference electrode, a counter electrode and a working or sensing electrode, to the latter of which a predetermined potential is applied, the presence of the analyte of interest generating a current signal which provides an indication of the presence of the analyte, in a well known manner.

Figure 6A:
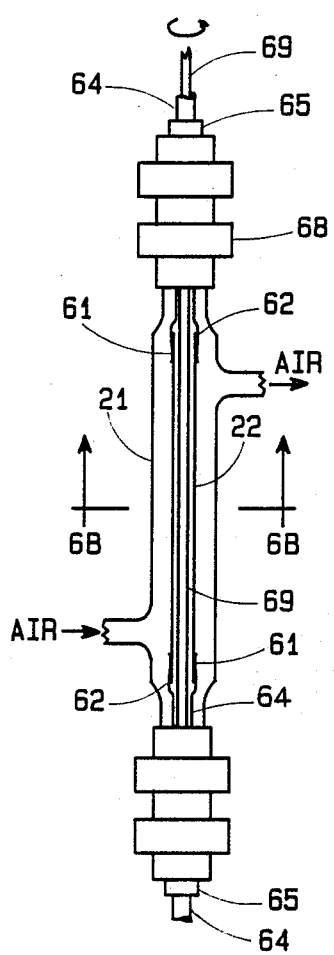
FIG. 6A is a side elevational view of a modified form of preconcentrator for use with the embodiment of FIG. 6.
Figure 6B:
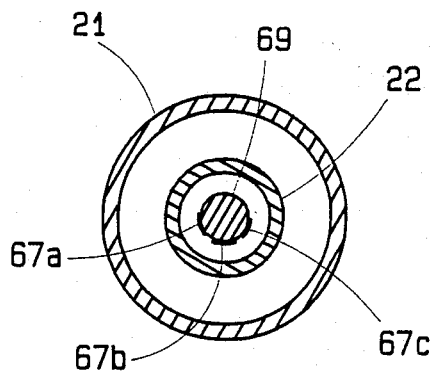
FIG. 6B is an enlarged view in transverse cross-section, taken along the line 68—68 in FIG. 6A.

In FIGS. 6A and 6B, there is illustrated a modified form of preconcentrator 15A, in which the air inlet and outlet of the gas-impermeable outer container 21 extend radially outwardly therefrom so as to foster a turbulent flow of air therethrough, while the inlet and outlet of the inner gaspermeable container 22 extend axially through the opposite ends of the outer container 21. More specifically, the opposite ends of the inner container 22, which may be formed of a porous Teflon tubing, are respectively coupled, as at 61, to tubes 62, which are formed of a suitable solid or nonporous material, such as solid Teflon. Each of the tubes 62 has a necked-down portion 64, which portions extend respectively coaxially outwardly through adapter tubes 65, which are respectively coupled to Swagelok unions 68. A solid cylindrical rod 69, made of quartz or other rigid, electrically non-conductive and chemically inert material, extends coaxially through the inner container 21, entering through one of the tubes 62, and having its distal end projecting a predetermined distanced into the necked-down portion 64 of the other tube 62, so that the tubes 62 respectively act as bearings for rotably supporting the rod 69 at spaced-apart locations. The outer end of the rod 69 is rotatable about its axis, as by a suitable motor (not shown). Fixed to the rod 69 are a plurality of microelectrodes, which may include a reference electrode 67a, a counter electrode 67b and a working electrode 67c, which extend outwardly through one of the tubes 62 for coupling to the amperometric sensor 66 by a suitable commutator or slip-ring arrangement (not shown).

It will be appreciated that, in operation, rotation of the rod 69 permits rotation of the microelectrodes 67a–67c within the inner container 22. This is advantageous, since it has been found that in certain applications more effective amperometric sensing of an analyte may be achieved when the microelectrodes are moved with respect to the analyte sample.

Figure 7:
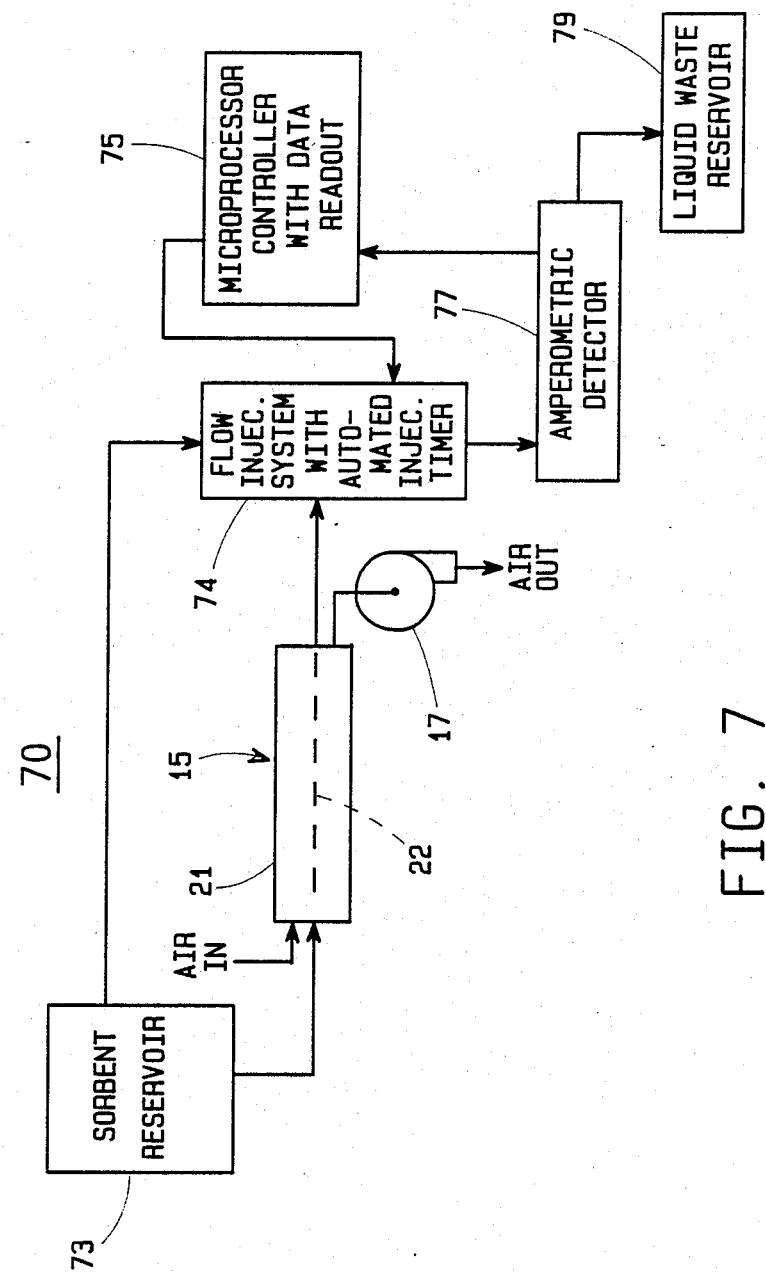
FIG. 7 is a functional block diagram of a still further embodiment of the invention utilizing amperometric detection.

In FIG. 7 there is illustrated an analytical system 70, which is a more detailed arrangement of the amperometric system 60. The system 70 includes the preconcentrator 15, the air outlet of which is coupled to the pump 17. The inlet end of the inner container 22 of the preconcentrator 15 is coupled to a sorbent reservoir 73, and its outlet end is coupled to a flow injection system 74 which includes an automated injection timer, and which is also coupled directly to the sorbent reservoir 73. A microprocessor controller 75 with data readout has an output coupled to the flow injection system 74. Sorbing liquid is passed from the flow injection system 74 to an amperometric detector 77, which generates an output signal in response to the presence of the analyte of interest, which signal is coupled to the microprocessor controller 75. After passing through the amperometric detector 77 the sorbing liquid passes to a liquid waste reservoir 79. Alternatively, the liquid exiting from detector 77 may be recalculated to reservoir 73.

In operation, analyte-sorbing liquid is injected from the sorbent reservoir 73 into the inner container 22 of the preconcentrator 70, where it absorbs the analyte of interest from the sampled air. When a sufficient amount of the analyte has been absorbed, the analyte-enriched sorbing liquid is passed from the preconcentrator 15 to the flow injection system 74, which in turn injects t into the amperometric detector 77 for detection. The sensitivity of the detector 77 may be affected by the flow therethrough. Accordingly, the sorbent reservoir 73 is directly connected to the flow injection system 74 for flowing the sorbing liquid continuously through the detector 77. Then, when it is desired to sense the preconcentrated analyte, which is typically after a predetermined time period, an automatic timer in the flow injection system 74 switches the flow to shut off the flow from the sorbent reservoir 73 and permit flow from the preconcentrator 15. After the desired volume of sorbing liquid has been passed to the detector 77, the timer again switches to shut off the flow from the preconcentrator 15, which has in the meantime been refilled with a new charge of sorbent for collection of another sample of analyte. The microprocessor controller 75 is responsive to the output signal from the detector 77 for varying the time periods set by the timer in the flow injection system 74. Thus, if the output signal is too low, the timer period between sample injections is increased, and it is decreased if the output signal is too high.

The amperometric systems of FIGS. 6–7 would be useful for the detection of chemically active compounds, such as hydrazine, methyl hydrazine and dimethyl hydrazine.

Figure 8:
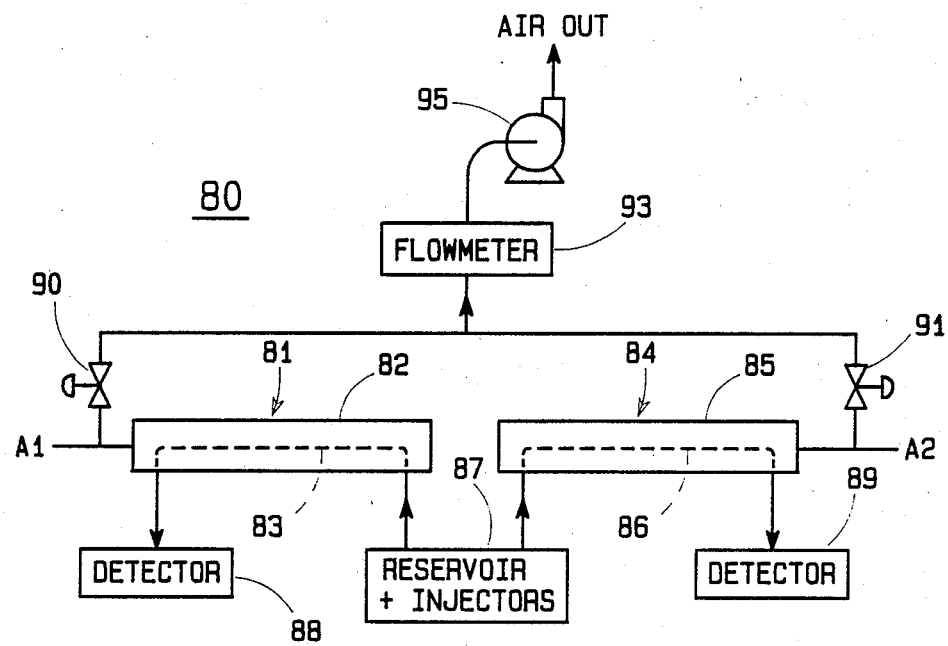
FIG. 8 is a functional block diagram of a calibration technique for the analytical systems of the present invention.

FIG. 8 illustrates a technique for calibrating the permeation absorption preconcentrator of the present invention. The technique utilizes a calibration system 80, which includes a first preconcentrator 81 having an outer container 82 and an inner container 83, and a second preconcentrator 84 having an outer container 85 and an inner container 86. The outer containers 82 and 85 are coupled in series between two air inlet/outlet ports A1 and A2. A sorbent reservoir 87 has two injectors which are respectively coupled to inlet ends of the inner containers 83 and 86, the outlet ends of which are respectively coupled to suitable detectors 88 and 89. The inlet/outlet ports A1 and A2 are respectively coupled through valves 90 and 91 to the inlet of a flow meter 93, the output of which is coupled to an air pump 95.

Essentially, the calibration technique comprises passing the sample gas through the series-connected preconcentrators 81 and 84, first in one direction and then in the other, and noting the readings of the detectors 88 and 89. More specifically, first the valve 90 is closed and the valve 91 is opened, and the sample medium is drawn through the preconcentrators 81 and 84 from left to right, as viewed in FIG. 8, by the pump 95, and the readings on the detectors 88 and 89 ar noted. These readings will presumably be different, since some of the analyte has been removed from the sample in the preconcentrator 8 and, therefore, the concentration should be less in the preconcentrator 84. Then, valve 91 is closed and valve 90 is opened, and the identical sample medium is drawn through the system in the opposite direction and the readings of the detectors 88 and 89 are again noted. The collection efficiencies $E_1$ and $E_2$ of the preconcentrators 81 and 84, respectively, are then related by the formulas:

$$E_1 = [c_{1f}c_{2r} - c_{1r}c_{2f}]/[c_{2r}(c_{1f} + c_{2f})]$$

and $$E_2 = [c_{1f}c_{2r} - c_{1r}c_{2f}]/[c_{1f}(c_{1r} + c_{2r})]$$

where $c_{1f}$ and $c_{2f}$ are, respectively, the readings of the detectors 88 and 89 during the first pass, and $c_{1r}$ and $c_{2r}$ are, respectively, the readings of the detectors 88 and 89 duing the second or reverse pass. These formulas are valid only if equal volumes of air are passed in both directions and if the volumes of liquid sorbent in preconcentrators 81 and 84 are the same.

Of course, the components of FIG. 8 can be interfaced with a microprocessor controller (not shown) so that the calibration could be automatically performed at programmed intervals.

Figure 9:
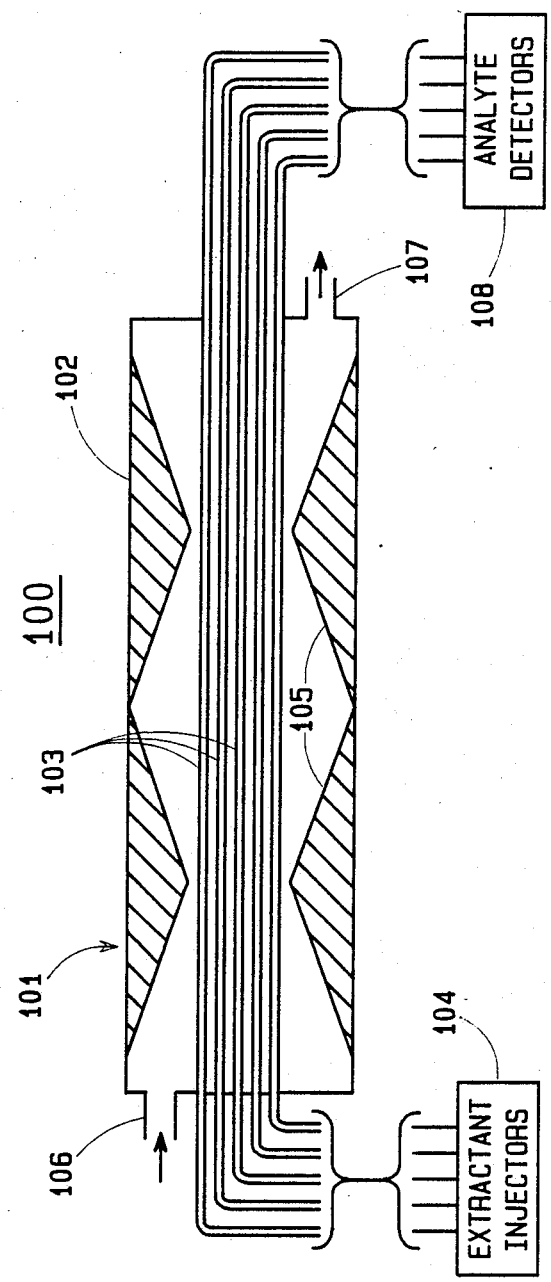
FIG. 9 is a partially structural and partially functional diagram of another embodiment of the invention utilizing a baffled permeation absorber and multiple gas permeable inner containers for simultaneous sampling of multiple analytes.

Referring now to FIG. 9, there is illustrate an analytical system 100, which permits the simultaneous detection of plural analytes in a gaseous medium. The system 100 includes a permeation absorption preconcentrator 101 which includes a gas-impermeable outer container 102 and a plurality of gas-permeable inner containers or tubules 103. The inner surface of the outer container 102 is provided with a plurality of baffles 105, which preferably extend circumferentially around the entire inner surface of the outer container 102. The baffles 105 are illustrated as being generally frustoconical in transverse cross section, but it will be appreciated that other shapes could be utilized. For example, a helical baffle arrangement could be used. The ends of the outer container 102 are closed except for an air inlet 106 at one end and an air outlet 107 at the other end, arranged for cooperation with the baffles 105 to enhance turbulent flow of the gaseous medium through the outer container 102. Alternatively, it will be appreciated that some of the baffles 105 could be eliminated and turbulent flow could be produced by arranging the air inlet and outlet 106 and 107 so that they extend radially from the outer container 102 respectively adjacent to the opposite ends thereof.

There are a plurality of extractant injectors 104 equal in number to the inner containers 103 and respectively coupled thereto for respectively injecting different sorbent materials thereinto for respectively absorbing different analytes of interest. Similarly, there are a plurality of analyte detectors 108 equal in number to the inner containers 103 and respectively coupled to the outlet ends thereof for separately sensing the analytes absorbed in the several inner containers 103.

It will be appreciated that the system 100 could be substituted for the preconcentrator 15 in any of the systems of FIGS. 2-7, described above.

While the preferred embodiments of the invention have been described in connection with the sampling of a gaseous medium, such as air, it will be appreciated that the principles of the present invention may also be utilized where the analyte is disposed in a liquid medium, such as in an aqueous solution. In such an arrangement, the inner container 22 of the preconcentrator 15 may be formed of microporous hollow tubes, made of a suitable material, such as polypropylene fibers, which are filled with a suitable hydrophobic organic extractant solvent, such as dodecane.

From the foregoing, it can be seen that there has been provided a simple, fast-acting and inexpensive analytical system for preconcentrating and detecting trace levels of analytes, such as hazardous materials, and which is uniquely adapted for use in portable deices, particularly automated or semi-automated devices for rapid on-site detection and quantification of such analytes. The system is adapted for use with multiple detection techniques, including photometric and amperometric techniques, while providing greater sensitivity, wider measurable concentration range and greater flexibility than prior devices using such techniques.

The embodiments of the invention in which an exclusive property or privilege is claimed are defined as follows:

1. A system for detecting traces of an analyte in a fluid medium comprising: permeation absorption preconcentrator means having a fluid-impermeable outer container and a fluid-permeable inner container, injection means for introducing analyte-sorbing material into said inner container, flow means for flowing the fluid medium through said outer container and around said inner container for trapping traces of analyte in said sorbing material, detection means coupled to said sorbing material containing traces of analyte trapped therein and responsive to the analyte for producing an output signal, and control means responsive to the output signal and coupled to said injection means and to said flow means for modulating the rates of flow of fluid medium and introduction of analyte-sorbing material to the preconcentrator means.

2. The system of claim 1, wherein the fluid medium is gaseous, and wherein said flow means includes pump means for moving the gaseous medium through said outer container, and flow meter means coupled to said pump means for sensing the rate of flow of gaseous medium through said pump means and producing a flow signal indicative thereof, said control means being coupled to said pump means and to said flow meter means for controlling the operations thereof in response to said flow signal.

3. The system of claim 1, wherein said injection means includes means for introducing an analyte-sorbing liquid into said inner container.

4. The system of claim 3, wherein said injection means includes means for introducing into said inner container a reagent responsive to the analyte for changing the light absorption or fluorescence or luminescence properties of said liquid, said detection means including a photometric sensor for sensing said light absorption or fluorescence or luminescence change.

5. The system of claim 4, wherein said photometric sensor includes fiber optic means coupled to at least one a light source and said light detection means, and extending into said inner container for transmitting light from said light source to the contents of said inner container and/or from the contents to said light detection means.

6. The system of claim 4, wherein said photometric sensor includes a light source for illuminating the contents of said inner container, and light detection means for measuring the absorption of light by the illuminated contents.

7. The system of claim 6, wherein said inner and outer containers are transparent or translucent to visible light, said photometric sensor including a light source disposed for illuminating said inner and outer containers and thereby the contents thereof, and light detection means disposed for measuring the light absorbed by the contents.

8. The system of claim 4, wherein tee reagent is responsive to the analyte to generate chemiluminescence, said detection means including light sensing means disposed for detecting the light emitted by said chemiluminescence.

9. The system of claim 1, wherein said detection means includes amperometric sensing means.

10. The system of claim 9, wherein said detection means includes electrodes disposed within said inner container.

11. The system of claim 10, and further comprising means for effecting movement of sad electrodes within said inner container.

12. The system of claim 1, and further comprising a calibration assembly for said preconcentrator means including a calibration permeation absorber substantially identical to said preconcentrator means and having a gasimpermeable outer container coupled in series with said outer container of said preconcentrator means and a gas-permeable inner container, calibration injection means for introducing analyte-sorbing material into the inner container of each of said preconcentrator and said calibration absorber, two calibration detectors respectively coupled to said inner containers and responsive to analyte absorbed in said sorbing material for respectively producing first and second output signals, and calibration flow means including valve means coupled for controlling the direction of flow of gaseous medium through said two series-connected outer containers and selectively operable so as to permit a gaseous medium to be passed therethrough first in one direction and then in the opposite direction.

13. The system of claim 1, wherein said injection means includes means for injecting plural analyte-sorbing materials into said inner container.

14. The system of claim 13, wherein said injection means includes means for introducing with each analytesorbing material a corresponding reagent for reacting with a particular analyte for producing a characteristic color or fluorescence or chemiluminescence, said detection means including photometric sensing means for detecting the produced color, fluorescence or luminescence.

15. The system of claim 1, wherein said outer container includes baffle means on an inner surface thereof to insure a turbulent flow of gaseous medium therethrough.

16. A system for detecting multiple analytes in a gaseous medium comprising: permeation absorption preconcentrator means having a gas-impermeable outer container and a plurality of gas-permeable inner containers, injection means for introducing a plurality of different analyte-sorbing materials respectively into said inner containers, flow means for flowing the gaseous medium through said outer container and around said inner containers for trapping different analytes respectively in said sorbing materials, detection means respectively coupled to said sorbing materials containing analytes trapped therein and responsive to the different analytes for respectively producing corresponding output signals, and control means responsive to said output signals and coupled to said injection means and to said flow means for modulating the rates of flow of fluid medium and introduction of analyte-sorbing material to the preconcentrator means.

17. The system of claim 16, wherein said injection means includes means for introducing with each of said analyte sorbing materials a corresponding reagent responsive to the corresponding analyte for producing a characteristic change, said detection means including photometric or amperometric sensing means for detecting the characteristic changes produced by each of said reagents.

18. The system of claim 16, wherein said analyte sorbing materials enter and exit said inner containers respectively near the ends of said outer container.

19. A system for detecting traces of an analyte in a gaseous medium comprising: permeation absorption preconcentrator means having a gas-impermeable outer container and a gas-permeable inner container, injection means for intermittently introducing charges of analyte-sorbing material into said inner container with each injected charge serving to remove from said inner container the previously-injected charge, flow means for flowing the gaseous medium through said outer container and around said inner container for trapping traces of analyte in said sorbing material, detection mean coupled to said sorbing material containing traces of analyte trapped therein and responsive to the analyte for producing an output signal, and timing and control means coupled to said injection means and to said flow means and to said detection means, said timing and control means being responsive to the output of said detection means for controlling the rate of flow of gaseous medium through said flow means and for controlling the time period between injections of analyte-sorbing material charges into said inner container so as to effect the trapping of a detectable amount of analyte in successive charges of said analyte-sorbing material in said inner container.

20. The system of claim 19, wherein said timing and control means includes a microprocessor operating under stored program control.

* * * * *